United States Patent
Hamanaka

(10) Patent No.: US 6,190,703 B1
(45) Date of Patent: *Feb. 20, 2001

(54) SUBLIMING PROPOLIS SOLID COMPOSITION AND PROCESS FOR THE PREPARATION THEREOF

(76) Inventor: Hiroyoshi Hamanaka, Room No. 105, 21st Bldg., 2nd Block, 1113-1, Oaza Murakami, Yachiyo-shi, Chiba (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/158,891

(22) Filed: Sep. 23, 1998

(30) Foreign Application Priority Data

Sep. 25, 1997 (JP) .................................... 9-259988

(51) Int. Cl.$^7$ .................................................. A61K 35/64
(52) U.S. Cl. ...................... 424/539; 424/76.2; 424/76.9
(58) Field of Search .................... 424/195.1, 49, 424/76.2, 76.8, 539, 76.9; 536/123.1, 124; 524/763

(56) References Cited

U.S. PATENT DOCUMENTS

| | | | |
|---|---|---|---|
| 4,649,046 | 3/1987 | Kross | 424/76 |
| 4,871,396 * | 10/1989 | Tsujita et al. | 106/286.8 |
| 5,561,116 * | 10/1996 | Nakamura et al. | 514/23 |

FOREIGN PATENT DOCUMENTS

| | | | |
|---|---|---|---|
| 212254 * | 6/1996 | (HU) | A61L/9/00 |
| 2-245159 | 10/1992 | (JP) . | |
| 98/29085 * | 7/1998 | (WO) | A61K/7/00 |

OTHER PUBLICATIONS

Klokova et al. HCAPLUS abstract for patent SU 1738284, searched on Nov. 30, 1998. AN: 1993:260694.*
Crisan et al. HCAPLUS abstract for patent RO 106658, searched Nov. 30, 1998. AN: 1998:398545. (Jun. 30, 1993).*

* cited by examiner

Primary Examiner—Ardin H. Marschel
Assistant Examiner—Marjorie A. Moran
(74) Attorney, Agent, or Firm—Nixon & Vanderhye

(57) ABSTRACT

A subliming propolis solid composition having a subliming function to stably give an excellent sense of fragrance and being useful as an atmosphere-ameliorating agent, the composition comprising (A) a propolis mass and/or an extraction residue thereof, (B) water alone or a mixture of water with a water-soluble solvent capable of forming a hydrogen bond with water, (C) a surfactant and (D) a hydrophilic polymer compound, the subliming propolis solid composition containing, per 100 parts by weight of total of the components (A) and (B), 0.01 to 25 parts by weight of the component (C) and 0.1 to 50 parts by weight of the component (D).

7 Claims, No Drawings

SUBLIMING PROPOLIS SOLID COMPOSITION AND PROCESS FOR THE PREPARATION THEREOF

FIELD OF THE INVENTION

The present invention relates to a subliming propolis solid composition, a process for the preparation thereof and an atmosphere-ameliorating agent. More specifically, it relates to a propolis solid composition which has a subliming function, stably gives an excellent sense of fragrance and is useful as an atmosphere-ameliorating agent, a process for the effective preparation thereof, and an atmosphere-ameliorating agent containing the same.

PRIOR ART OF THE INVENTION

Propolis which has been known as a natural antimicrobial substance or a health-improving substance is a composition containing secondary metabolites typified by flavonoids and phenols produced by phanerogams such as aspen and pine trees and collected by arthropods such as honeybees in wax and salivary juice which are produced by the arthropods. When it is attempted to use it for a food, it is too hard to eat. Generally, it is therefore converted to a liquid food prepared by an extraction method using ethyl alcohol or liquefied carbon dioxide gas, or an extract is mixed with water-soluble polysaccharide and the mixture is served as a solid food easily decomposable by salivary juice.

However, the basic principle of the above extraction method is a nonselective extraction using a good solvent, and a wax which is not considered to essentially serve as the antimicrobial function or the health-improving function is also co-extracted. The extract therefore contains a useless component, and its insolubility in water is strengthened so that it is brought into a hard-to-eat state and is unstable in an aqueous solution. There is therefore a problem that even when it is employed for daily use articles, generally, the use thereof is inevitably extremely limited.

In the field of foods, there is employed a method in which water-soluble components alone are extracted by bringing a propolis mass into contact with water, to prepare an edible food product. However, the above method is not at all satisfactory as far as its performances are concerned, since no oil-soluble active components can be extracted and since the amount of water-soluble components that are extracted is small.

Under these circumstances, as a method for satisfying both the component extraction performance and edibility, the present inventor proposed a propolis food composition and a process for the preparation thereof according to a so-called micelle extraction method utilizing a hydrophilic micelle solution formed by the use of a polyol-fatty acid ester surfactant (JP-B-4-66544). The above method not only permits the preparation of an edible propolis food, but also permits the preparation of a liquid propolis food containing useful water-soluble and oil-soluble components but not containing useless wax components according to a separated and selective extraction mechanism.

However, a characteristic odor is strengthened in the above propolis extract, and it is difficult to use the extract for daily use articles which are inevitably in contact with the atmosphere.

As a propolis solid composition, a candy prepared by sealing a propolis extract in a solid malt sugar having a low molecular weight and a tablet product prepared by impregnating a water-insoluble cellulose with a propolis extract are available. However, these propolis compositions are prepared from the above liquid propolis food on the basis of only an advantage that they are suitable for being carried with, and they have no subliming function. Their odor has an adverse effect, and when they are taken alone, they are not suitable for use in any fields other than foods.

SUMMARY OF THE INVENTION

It is an object of the present invention to provide a propolis solid composition which has a subliming function, stably gives an excellent sense of fragrance and is useful as an atmosphere-ameliorating (air freshening) agent, a process for the effective production thereof, and an atmosphere-ameliorating (air freshening) agent containing the same.

For achieving the above object, the present inventor has made diligent studies, and as a result, has found the following. A solid composition containing a propolis mass and/or its extraction residue, water or a mixture of water with a specific water-soluble solvent, a surfactant and a hydrophilic polymer compound in a specific amount ratio has a subliming function in continuously dissipating, little by little, an active component derived from propolis as a natural antimicrobial and health-improving substance, stably gives an excellent sense of fragrance and is useful as an atmosphere-ameliorating agent. Further, the above propolis solid composition can be effectively prepared by homogeneously dispersing a propolis mass and/or an extraction residue thereof in a solution obtained by micelle-dissolving a surfactant in water or a mixture of water with a specific water-soluble solvent to obtain a dispersion, and adding and homogeneously mixing a hydrophilic polymer compound to and with the dispersion. On the basis of the above finding, the present invention has been completed.

According to the present invention, there is provided a subliming propolis solid composition containing (A) a propolis mass and/or an extraction residue thereof, (B) water alone or a mixture of water with a water-soluble solvent capable of forming a hydrogen bond with water, (C) a surfactant and (D) a hydrophilic polymer compound, the subliming propolis solid composition containing, per 100 parts by weight of total of the components (A) and (B), 0.01 to 25 parts by weight of the component (C) and 0.1 to 50 parts by weight of the component (D).

According to the present invention, further, there is provided an atmosphere-ameliorating agent containing the above subliming propolis solid composition.

Further, according to the present invention, there is provided a process for the preparation of a subliming propolis solid composition, which comprises micelle-dissolving (C) a surfactant in (B) water alone or a mixture of water with a water-soluble solvent capable of forming a hydrogen bond with water, to obtain a solution, mixing the solution with (A) a propolis mass and/or an extraction residue thereof so as to be brought into contact with each other, to form a dispersion, and then adding and homogeneously mixing (D) a hydrophilic polymer compound to/with the dispersion.

DESCRIPTION OF PREFERRED EMBODIMENTS

In the present invention, the component (A) includes a propolis mass, an extraction residue obtained by subjecting a propolis mass to extraction according to various methods or a mixture of a propolis mass with a propolis extraction residue. The propolis mass is not specially limited, and it can be any propolis, e.g., originated in Brazil, U.S.A., Germany, China, or the like.

Further, the above propolis extraction residue is not specially limited, and a residue obtained by subjecting a propolis mass to extraction according to a known method can be used. Examples of the propolis extraction residue include a propolis residue obtained by subjecting a propolis mass to extraction with water, ethyl alcohol or liquefied carbon dioxide gas; and a propolis extraction residue having a surface on which part of a surfactant is adsorbed, which is obtained by bringing a system prepared by micelle-dissolving a polyol-fatty acid surfactant in a solvent having a plurality of OH groups and a propolis mass into contact with each other and removing uniformly dissolved soluble components according to the method disclosed in JP-B-4-66544.

In the present invention, as component (B), water alone or a mixture of water with a water-soluble solvent capable of forming a hydrogen bond with water is used. Examples of the water-soluble solvent capable of forming a hydrogen bond with water include alcohol-based solvents such as methyl alcohol, ethyl alcohol, n-propyl alcohol, isopropyl alcohol, ethylene glycol, diethylene glycol, propylene glycol, dipropylene glycol, 1,3-butylene glycol, glycerin, ethylene glycol monomethyl ether, ethylene glycol monoethyl ether, ethylene glycol monopropyl ether, ethylene glycol monoisopropyl ether, ethylene glycol monobutyl ether, diethylene glycol monomethyl ether, diethylene glycol monoethyl ether, diethylene glycol monopropyl ether, diethylene glycol monoisopropyl ether, diethylene glycol monobutyl ether, propylene glycol monomethyl ether, propylene glycol monoethyl ether, propylene glycol monopropyl ether, propylene glycol monoisopropyl ether, propylene glycol monobutyl ether, dipropylene glycol monomethyl ether, dipropylene glycol monoethyl ether, dipropylene glycol monopropyl ether, dipropylene glycol monoisopropyl ether and dipropylene glycol monobutyl ether; ether solvents such as ethylene glycol dimethyl ether, ethylene glycol diethyl ether, diethylene glycol dimethyl ether, diethylene glycol diethyl ether, furfural and dioxane; ketone solvents such as acetone and methyl ethyl ketone; and nitrogen-containing solvents such as 2-methylimidazolidinone. The above water-soluble solvents may be used alone or in combination.

In the present invention, the surfactant (C) is not specially limited, and it can be selected from anionic, nonionic, cationic and amphoteric surfactants.

Examples of the above anionic surfactant include alkylarylsulfonic acid salts; soaps such as sodium salts, potassium salts and triethanolamine salts of various fatty acids; sulfuric acid ester salts such as alkylsulfuric acid salts and alkyl polyoxyalkylene ether sulfuric acid salt; phosphoric acid ester salts such as alkylphosphoric acid ester salt, alkylarylphosphoric acid ester salt, alkyl polyoxyalkylene ether phosphoric acid ester salt and alkylaryl polyoxyalkylene ether phosphoric acid ester salt; and polysoaps such as polystyrene sulfonate and polyacrylate. These surfactants may be used alone or in combination.

Examples of the nonionic surfactant include fatty acid esters such as sorbitan fatty acid ester, polyoxyethylene sorbitan fatty acid ester, glycerin fatty acid ester, diglycerin fatty acid ester, triglycerin fatty acid ester, tetraglycerin fatty acid ester, pentaglycerin fatty acid ester, hexaglycerin fatty acid ester, ethylene glycol fatty acid ester, polyoxyethylene glycol fatty acid ester, sucrose fatty acid ester and di(glycerin)borate fatty acid ester; polyethers such as alkylene polyoxyalkylene ether, alkylaryl polyoxyalkylene ether, polyoxyethylene glycol-polyoxypropylene glycol block copolymer; tertiary amines such as N,N-di (polyoxyalkylene)alkylamine and N,N,N',N'-tetra(polyoxyalkylene)ethylenediamine; and amides such as fatty acid monoalkylolamide and fatty acid dialkylolamide. The above nonionic surfactants may be used alone or in combination.

Examples of the cationic surfactant include quaternary ammonium salts such as tetralkylammonium salt, trialkyl (β-hydroxyalkyl)ammonium salt and dialkyldi(polyoxyalkylene)ammonium salt. These cationic surfactants may be used alone or in combination. Further, examples of the amphoteric surfactant include betaines such as trialkylbetaine and alkylimidazolinebetaine, and phospholipid such as lecithin. These amphoteric surfactants may be used alone or in combination.

In the present invention, the surfactant as a component (C) is particularly preferably a high-molecular-weight anionic surfactant containing carboxylic acid salt.

In the present invention, examples of the hydrophilic polymer compound as a component (D) include carrageenan, agar, starch, polyvinyl alcohol, polyacrylamide, polyethylene oxide, carboxymethyl cellulose, guar gum, xanthane gum, crosslinked polyacrylate and crosslinked polyacrylamide. These compounds may be used alone or in combination. Carageenan is particularly preferred.

The subliming propolis solid composition of the present invention comprises the above component (A), component (B), component (C) and component (D), and the content of the surfactant as a component (C), per 100 parts by weight of the total of the components (A) and (B), is 0.01 to 25 parts by weight. When the above content of the component (C) is less than 0.01 part by weight, it is difficult to stably disperse the component (A). When the above content exceeds 25 parts by weight, the subliming function of active components derived from propolis is extremely inhibited. In view of the dispersing stability of the component (A) and the subliming function of the active component, the above content of the component (C) is preferably 0.1 to 5 parts by weight, particularly preferably 0.5 to 2 parts by weight.

The content of the hydrophilic polymer compound as a component (D) per 100 parts by weight of the total of the components (A) and (B) is 0.1 to 50 parts by weight. When the above content of the component (D) is less than 0.1 part by weight, it is difficult to solidify the composition. When the above content exceeds 50 parts by weight, the subliming function of the component derived from propolis is extremely inhibited. In view of the solidification of the composition and the subliming function of the active component, the above content of the component (D) per 100 parts by weight of the total of the components (A) and (B) is preferably 0.5 to 10 parts by weight, particularly preferably 1 to 5 parts by weight.

Further, the component (A):component (B) weight ratio is preferably in the range of from 1:999 to 1:2. When the amount of the component (A) is smaller than the above range, the active component derived from propolis may be too small to achieve the object of the present invention. When the amount of the component (A) is larger than the above range, the dispersing stability of the component (A) is liable to be poor. The component (A):component (B) weight ratio is more preferably in the range of from 1:99 to 1:4, particularly preferably 1:49 to 1:9.

The process for the preparation of the subliming propolis solid composition, provided by the present invention, will be explained hereinafter.

In the process of the present invention, first, a surfactant as a component (C) is added to water alone or a mixture of water with the above water-soluble solvent as a component (B), and micelle-dissolved therein. Further, a propolis mass and/or an extraction residue thereof as a component (A) are/is added. Otherwise, a propolis mass and/or an extraction residue thereof as a component (A) are/is added concurrently with the surfactant. When a propolis mass extraction residue on which a surfactant is adsorbed is used as an extraction residue of a propolis mass, it may not be required to add a surfactant as a component (C) in some cases although it should be determined depending upon the kind and amount of the above surfactant.

The propolis mass and/or the extraction residue thereof are/is added as described above, followed by mixing at a temperature of preferably 15 to 200° C., particularly preferably 15 to 100° C. so as to bring it or them and the solvent into contact with each other, to prepare a dispersion. Then, the dispersion is maintained as prepared, cooled or heated, preferably maintained at a temperature of preferably 0 to 200° C., particularly preferably 0 to 100° C., the hydrophilic polymer compound as a component (D) is added thereto, and the resultant composition is allowed to stand.

In the above case, the above composition may be allowed to stand in a production apparatus to form a solid composition before the solid composition is withdrawn. Otherwise, the above composition may be withdrawn from the apparatus as it is in a liquid state, then placed in a packaging container and allowed to stand therein to form a solid composition.

On the other hand, when a propolis mass and/or an extraction residue thereof are/is replaced by a propolis extract prepared according to the micelle extraction method disclosed in JP-B-4-66544, and the hydrophilic polymer compound is added to, and homogeneously mixed with, the propolis extract in the same manner as in the process for the preparation of a subliming propolis solid composition in the present invention, no desirable product can be obtained in view of its production and its application for use, since no homogeneous solid composition is obtained and since a separated liquid which results dissipates an extreme odor.

The subliming propolis solid composition of the present invention is remarkably useful for healthy living since it functions as an atmosphere-ameliorating agent which shuts off an offensive odor and gives a pleasant sense of fragrance owing to co-operative activities of contained components when brought into contact with ambient atmosphere as it is or used together with a device such as a fan.

The subliming propolis solid composition of the present invention may contain various additives such as a colorant, an antiseptic, an antioxidant and an aromatic so long as the object of the present invention is not impaired.

EXAMPLES

The present invention will be explained more in detail with reference to Examples and Application Examples hereinafter, while the present invention shall not be limited by these Examples.

Example 1

A closed reactor having a stirrer, a thermometer and a heating device was charged with 90 parts by weight of water, 5 parts by weight of glycerin, 1 part by weight of tetraglycerin monooeleate and 0.01 part by weight of sodium polyacrylate having an average polymerization degree of 5,000, and the mixture was stirred under atmospheric pressure at 40° C. for 20 minutes to obtain a homogeneous solution. Then, to the solution was added 5 parts by weight of a propolis mass originated in Brazil, and the solution and the propolis mass were stirred at 30 to 40° C. to be brought into contact with each other, to prepare a dispersion. To the dispersion was added 2.5 parts by weight of carrageenan (trade name "Soageena" WX-560, supplied by MRC Polysaccharide K.K.), the mixture was temperature-increased up to 60° C. with stirring, to form a homogenous mixture, and at 50 to 60° C., the homogeneous mixture was withdrawn from the reactor. Then, the mixture was allowed to stand at 20° C. for 24 hours, to give a dark brown subliming propolis solid composition.

The above composition was placed in a container with its top open, and evaluated for a form thereof and a state of an odor from its surface after it was allowed to stand at 20° C. for 1 day and after it was allowed to stand at 20° C. for 30 days. Table 1 shows the results.

Comparative Example 1

A homogeneous solution containing 90 parts by weight of water, 5 parts by weight of glycerin, 1 part by weight of tetraglycerin monooeleate and 0.01 part by weight of sodium polyacrylate having an average polymerization degree of 5,000 was prepared, and 5 parts by weight of a propolis extract (containing 10% by weight of water as an extracting solvent, 89% by weight of glycerin and 1% by weight of tetraglycerin monooleate) was further added to the above solution. To the resultant solution was added 2.5 parts by weight of the same carrageenan as that used in Example 1, and the solution and the carrageenan were homogeneously mixed in the same manner as in Example 1. The resultant mixture was allowed to stand at 20° C. for 4 hours, to give a solid composition.

The above solid composition was evaluated in the same manner as in Example 1. Table 1 shows the results.

TABLE 1

| | After standing at 20° C. for 1 day | | After standing at 20° C. for 30 days | |
| --- | --- | --- | --- | --- |
| | Form | Surface odor | Form | Surface odor |
| Ex. 1 | Homogeneous solid | Fragrant aroma | Homogeneous solid | Fragrant aroma |
| CEx. 1 | Liquid distributed on surface | Irritant odor | Separated into upper layer of liquid and lower layer of solid | Irritant odor |

Ex. = Example, CEx. = Comparative Example

Table 1 shows that the composition obtained in Example 1 has components correctly formed into a composite and works its subliming function as to give an ameliorated atmosphere.

Example 2

A closed reactor having a stirrer, a thermometer, a heater and a condenser was charged with 90 parts by weight of water and 0.01 part by weight of potassium polyacrylate having an average polymerization degree of 3,000, and the mixture was stirred at 15° C. for 30 minutes. Then, to the resultant solution was added 10 parts by weight of a propolis mass originated in Brazil, and the solution and the propolis mass were mixed so as to be brought into contact with each other under a pressure of 5 kg/cm² at 95 to 100° C. for 3 hours, to prepare a dispersion.

Then, the temperature inside the reactor was decreased to 0° C., and the dispersion as a whole was re-charged into other open reactor. To the dispersion was added 3 parts by weight of crosslinked sodium polyacrylate (trade name: Viscomate PX-112, supplied by Showa Denko K.K.), and the dispersion and the crosslinked sodium polyacrylate were homogeneously mixed to give a dark brown subliming propolis solid composition.

The above composition was evaluated in the same manner as in Example 1. Table 2 shows the results.

Comparative Example 2

3 Parts by weight of the same crosslinked sodium polyacrylate as that used in Example 2 was added to a solution of 10 parts by weight of a propolis extract (extracting solvent: ethyl alcohol) in a uniform solution containing 90 parts by weight of water and a 0.01 part by weight of potassium polycarylate having an average polymerization degree of 3,000, and the mixture was treated in the same manner as in Example 2 to give a solid composition.

The above composition was evaluated in the same manner as in Example 1. Table 2 shows the results.

TABLE 2

|  | After standing at 20° C. for 1 day | | After standing at 20° C. for 30 days | |
| --- | --- | --- | --- | --- |
|  | Form | Surface odor | Form | Surface odor |
| Ex. 2 | Uniform granular solid | Fragrant aroma | Granules decreased in size by about 30% by sublimation | Fragrant aroma |
| CEx. 2 | Liquid distributed on place to place | Irritant odor | Liquid film formed on surface | Odor intensified |

Ex. = Example, CEx. = Comparative Example

Table 2 shows that the composition obtained in Example 2 has components correctly formed into a composite and well works its subliming function.

Examples 3–8

Subliming propolis solid compositions were prepared from components (A), components (B), components (C) and components (D) shown below in the same manner as in Example 1 or 2.

Components (A), (B), (C) and (D) and Preparation Methods Used in Examples 3 to 8

Example 3

Component (A): 7 parts by weight of propolis mass originated in Brazil.

Component (B): 80 parts by weight of water, 10 parts by weight of ethyl alcohol and 3 parts by weight of diethylene glycol monomethyl ether.

Component (C): 1 part by weight of ammonium poly(10) oxyethylene nonyl phenyl ether phosphate, 1 part by weight of N,N-di[poly(5)oxyethylene]laurylamine, and 0.2 part by weight of a styrene-sodium maleate copolymer having an average polymeization degree of 2,000.

Component (D): 4 parts by weight of carrageenan (Soageena WX-560, supplied by MRC Polysaccharide K.K.) and 1 part by weight of guar gum.

Preparation method: according to the method in Example 1.

Example 4

Component (A): 4 parts by weight of propolis mass originated in Brazil.

Component (B): 90 parts by weight of water, 3 parts by weight of dioxane and 3 parts by weight of ethylene glycol dimethyl ether.

Component (C): 0.3 part by weight potassium oleate, 1.2 parts by weight of poly(8)oxyethylene octylphenyl ether, 0.5 part by weight sodium laurylsulfate and 0.5 part by weight of methyl methacrylate-potassium methacrylate (molar ratio 9:1) copolymer.

Component (D): 5 parts by weight of carrageenan (Soageena WX-560, supplied by MRC Polysaccharide K.K.), 0.3 part by weight of xanthane gum and 0.2 part by weight of carboxymethyl cellulose.

Preparation method: according to the method in Example 1.

Example 5

Component (A): 10 parts by weight of propolis mass originated in U.S.A.

Component (B): 84 parts by weight of water, 5 parts by weight of 1,3-butylene glycol and 1 part by weight of acetone.

Component (C): 24 parts by weight of a block copolymer in which polyethylene glycol having an average molecular weight of 2,000 was block-polymerized to each side of polypropylene glycol having an average molecular weight of 2,000 and 1 part by weight of acrylamide-sodium acrylate (molar ratio 1:4) copolymer having an average polymerization degree of 6,000.

Component (D): 3 parts by weight of carrageenan (Soageena WX-560, supplied by MRC Polysaccharide K.K.), 1 part by weight of starch and 2 parts by weight of guar gum.

Preparation method: according to the method in Example 1.

Example 6

Component (A): 1 part by weight of propolis mass originated in China.

Component (B): 99 parts by weight of water.

Component (C): 0.01 parts by weight of sodium polycarylate having an average polymerization degree of 6,000.

Component (D): 1 part by weight of carrageenan (Soageena MW-280, supplied by MRC Polysaccharide K.K.), 29 parts by weight of 70% polyvinyl alcohol having an average polymerization degree of 500 and 20 parts by weight of polyethylene oxide having an average polymerization degree of 2,000.

Preparation method: according to the method in Example 1.

Example 7

Component (A): 20 parts by weight of propolis mass originated in Brazil.

Component (B): 78 parts by weight of water, 1 part by weight of isopropyl alcohol, 0.5 part by weight of furfural and 0.5 part by weight of 2-methylimidazolidinone.

Component (C): 0.1 part by weight of dihexadecyl-dimethylammonium chloride, 0.1 part by weight of dodecyldimethylbetaine, 0.2 part by weight of lecithin and 0.6 part by weight of ammonium polyacrylate having an average polymerization degree of 1,000.

Compound (D): 0.05 part by weight of carrageenan (Soageena MM-501, supplied by MRC Polysaccharide K.K.) and 0.05 part by weight of purified agar powder.

Preparation method: according to the method in Example 1.

Example 8

Component (A): 5 parts by weight of propolis mass originated in China.

Component (B): 90 parts by weight of water and 5 parts by weight of methanol.

Component (C): 0.8 part by weight of poly(10)-oxyethylene glycol monolaurate and 0.2 part by weight of an acrylamide-sodium acrylate (molar ratio 1:9) copolymer having an average polymerization degree of 4,000.

Component (D): 0.01 part by weight of carrageenan (Soageena WX-560, supplied by MRC Polysaccharide K.K.), 0.02 part by weight of crosslinked sodium polyacrylate (Viscomate PX-112, supplied by Showa Denko K.K.) and 0.07 part by weight of crosslinked sodium polyacrylate-polyacrylamide copolymer (Magic Crystal 800, made in Taiwan).

Preparation method: according to the method in Example 2.

The above compositions were placed in closed containers, allowed to stand at 20° C. for 30 days, and then evaluated for forms and odors on surfaces. Table 3 shows the results.

TABLE 3

| | After standing at 20° C. for 30 days | |
| --- | --- | --- |
| Example | Form | Odor on surface |
| 3 | Uniform solid | Fragrant aroma |
| 4 | " | " |
| 5 | " | " |
| 6 | " | " |
| 7 | " | " |
| 8 | " | " |

Table 3 shows that the compositions obtained in Examples 3 to 8 have excellent performances.

Example 9

A solution containing 1 part by weight of sorbitan monolaurate and 100 parts by weight of glycerin and 5 parts by weight of a propolis mass originated in Brazil were kept in contact with each other under heat at 60 to 70° C. for 1 hour, and a portion which was uniformly dissolved by micellisation and solvent extraction was removed, to obtain a propolis extraction residue.

An open reactor having a stirrer, a thermometer, a heater and a condenser was charged with the above propolis extraction residue (composite formed of 6 parts by weight of propolis residue, 0.04 part by weight of sorbitan monolaurate and 4 parts by weight of glycerin both of which were adhering thereto), and then further charged with 85 parts by weight of water, 5 parts by weight of ethyl alcohol and 0.01 part by weight of sodium polyacrylate having an average polymerization degree of 5,000, followed by homogeneous mixing under atmospheric pressure at 20° C. Then, to the resultant mixture was added 5 parts by weight of carrageenan (Soageena WX-560, supplied by MRC Polysaccharide K.K.), and the mixture was temperature-increased up to 60° C. Then, the mixture was withdrawn from the reactor at the above temperature and allowed to stand at 20° C. for 24 hours, to give a dark brown subliming propolis solid composition.

The above composition was evaluated in the same manner as in Example 1. Table 4 shows the results.

Example 10

A solution containing 1 part by weight of tetraglycerin monooleate and 100 parts by weight of propylene glycol and 5 parts by weight of a propolis mass originated in China were kept in contact with each other under heat at 60 to 70° C. for 30 minutes, and a portion which was uniformly dissolved by micellisation and extraction was removed, to obtain a propolis extraction residue.

An open reactor having a stirrer was charged with the above propolis extraction residue (composite formed of 9 parts by weight of propolis residue, 0.01 part by weight of tetraglycerin monooleate and 1 part by weight of propylene glycol both of which were adhering thereto), and then charged with 90 parts by weight of water, followed by stirring at 20° C. to form a homogeneous mixture. Then, to the mixture was added 3 parts by weight of crosslinked sodium polyacrylate (trade name: Viscomate PX-112, supplied by Showa Denko K.K.), following by homogeneous mixing for 15 minutes, to give a brown subliming propolis solid composition.

The above composition was evaluated in the same manner as in Example 1. Table 4 shows the results.

TABLE 4

| | After standing at 20° C. for 1 day | | After standing at 20° C. for 30 days | |
| --- | --- | --- | --- | --- |
| | Form | Surface odor | Form | Surface odor |
| Ex. 9 | Uniform solid | Fragrant aroma | Uniform solid decreased in size by about 20% by sublimation | Fragrant aroma |
| Ex. 10 | Uniform granular solid | Fragrant aroma | Granules decreased in size by about 30% by sublimation | Fragrant aroma |

Ex. = Example

Table 4 shows that the compositions obtained in Examples 9 and 10 have components correctly formed into composite and allow their subliming functions to reliably work.

Application Example 1

There were selected 120 men and women having ages of 20 to 60 at random from people who drive cars, as participants in tests.

The subliming propolis solid compositions obtained in Examples 1 to 10 and the solid compositions obtained in Comparative Examples 1 and 2 in an amount of 100 g each were filled in open-topped containers having a diameter of 6 cm and a height of 6 cm, and fixed in central portions of front seats of testing 1,800 to 3,000 cc-displacement cars. And, a panel test was conducted with regard to the sense of an odor and the driving mood according to the following procedures. Table 5 shows the results.

(1) Sense of odor

A composition was fixed in a testing car which had been driven for an average of 3 hours a day over the period of at least 1 year, all the doors and windows were closed, and the car was allowed to stand without any driver under an ambient temperature condition for 24 hours. Then, the door on the front seat side was opened, and 10 panelists smelled an odor in the car to give answers.

(2) Driving mood

A composition was fixed in a testing car which had been driven for an average of 3 hours a day over the period of at least 1 year, all the doors and windows were closed, and the car was allowed to stand without any driver under an ambient temperature condition for 24 hours. Then, a panelist drove the car for 3 hours (driving for 1 hour and 15 minutes→standing for 30 minutes→driving 1 hour and 15 minutes) to give an answer. Ten panelists were drove cars under the same conditions as above to give answers.

TABLE 5

| Sample | Sense of an odor*1 | Driving mood*2 |
| --- | --- | --- |
| Example 1 | A | ⊙ |
| Example 2 | A | ⊙ |
| Example 3 | A | ⊙ |
| Example 4 | A | ⊙ |
| Example 5 | A | ⊙ |
| Example 6 | A | ⊙ |
| Example 7 | A | ⊙ |
| Example 8 | A | ⊙ |
| Example 9 | A | ⊙ |
| Example 10 | A | ⊙ |
| Comparative Example 1 | D | Δ |
| Comparative Example 2 | D | Δ |

Notes: *1The evaluation standard of the sense of an odor is as follows.

A: All of 10 panelists agree that the odor which existed inside the car before has been replaced with a pleasant odor.

B: One to three panelists out of 10 feel that the odor which remained inside the car before does not change, and 9 to 7 panelists say that the odor which existed before has been replaced with a pleasant odor.

C: Four to six panelists out of 10 feel that the odor which remained inside the car before does not change, and 6 to 4 panelists say that the odor which existed before has been replaced with a pleasant odor.

D: Seven to nine panelists out of 10 feel that the odor inside the car is too intense and undesirable, and 3 panelists or less feel that the odor inside the car is not unpleasant.

*2 The evaluation standard of the driving mood is as follows.

⊙ All of 10 panelists agree that driving has been more pleasant than before.

○ Seven to nine panelists out of 10 say that driving has been more pleasant than before.

Δ Six panelists or less out of 10 say that driving has been more pleasant than before.

Table 5 clearly shows that the subliming propolis solid composition of the present invention gives the sense of pleasant odor and a pleasant driving mood so that it is remarkably excellent as an atmosphere-ameliorating agent inside cars.

Application Example 2

There were selected 120 men and women having ages of 20 to 60 at random from people who have chronic rhinitis, as participants in tests.

The subliming propolis solid compositions obtained in Examples 1 to 10 and the solid compositions obtained in Comparative Examples 1 and 2 in an amount of 300 g each were filled in cylindrical containers having a diameter of 7.2 cm and a height of 8.8 cm each and having a hole having a diameter of 2.2 cm in the center of top each. The containers were respectively attached to a fan housing a motor and a scirocco fan (AIR FRESSURE, 8.5 cm×9 cm×24, made in Taiwan), and a panel test was carried out with the sense of an odor and a feeling in breathing in a state where the container was fixed 50 cm away from a pillow and the fan was in operation for an average of 8 hours a day during the sleep time of each participant, according to the following procedures. Table 6 shows the results.

(1) Sense of odor

Fifteen minutes after the initiation of operation of a fan with a composition the container on a first day, 10 panelists smelled an odor around pillows before they fell asleep, to give answers.

(2) Feeling in breathing

Fans with a composition in the container was operated for an average of 8 hours a night for 30 days, and on a 30th day, 10 participant took a deep breath to give answers.

TABLE 6

| Sample | Sense of an odor*1 | Feeling in breathing*2 |
| --- | --- | --- |
| Example 1 | A | ⊙ |
| Example 2 | A | ⊙ |
| Example 3 | A | ⊙ |
| Example 4 | A | ⊙ |
| Example 5 | A | ⊙ |
| Example 6 | A | ⊙ |
| Example 7 | A | ⊙ |
| Example 8 | A | ⊙ |
| Example 9 | A | ⊙ |
| Example 10 | A | ⊙ |
| Comparative Example 1 | D | Δ |
| Comparative Example 2 | D | Δ |

Notes: *1The evaluation standard of the sense of an odor is as follows

A: All of 10 panelists agree that the composition give a pleasant odor.

B: One to three panelists out of 10 say that the odor is too intense, and 9 to 7 panelists say that a pleasant odor is given.

C: Four to six panelists out of 10 say that the odor is too intense and is unpleasant, and 6 to 4 panelists say that the odor is not so intense.

D: Seven to nine panelists out of 10 say that the odor is too intense and is unpleasant, and 3 panelists or less say that the odor is not so intense.

*2: The evaluation standard of the feeling in breathing is as follows.

⊙ All of 10 panelists agree that breathing has been more pleasant than breathing before the fan was provided and operated.

○ Seven to nine panelists say that breathing has been more pleasant than breathing before the fan was provided and operated.

Δ Six panelists or less say that breathing has been more pleasant than breathing before the fan was provided and operated.

Table 6 clearly shows that the subliming propolis solid composition of the present invention is pleasant in the sense of an odor and the feeling in breathing and is therefore excellent as an agent for ameliorating an indoor atmosphere.

Application Example 3

The subliming propolis solid compositions obtained in Examples 1 to 10 and the solid compositions obtained in Comparative Examples 1 and 2 were respectively cut to a size of 2 cm×2 cm×0.5 cm, and the so-prepared pieces were attached to central portions of standard agar flat plate culture media and central portions of desoxycolate agar culture media, respectively. General microorganisms and *Escherichia coli* were cultured.

Further, as a control, general microorganisms and *Escherichia coli* were cultured without attaching the above propolis solid composition to the agar plate. Table 7 shows the results.

TABLE 7

| Sample | Cultured microorganisms | |
|---|---|---|
| | General microorganism | *Escherichia coli* |
| Control | Propagating all over the plate surface | Propagating all over the plate surface |
| Example 1 | No microorganism on and around the solid composition, and less-degree of propagation as a whole | No microorganism on and around the solid composition, and less-degree propagation as a whole |
| Example 2 | " | " |
| Example 3 | " | " |
| Example 4 | " | " |
| Example 5 | " | " |
| Example 6 | " | " |
| Example 7 | " | " |
| Example 8 | " | " |
| Example 9 | " | " |
| Example 10 | " | " |
| Comparative Example 1 | Less-degree propagation on and around the solid composition, but high-degree propagation as a whole | Less-degree propagation on and around the solid composition, but high-degree propagation as a whole |
| Comparative Example 2 | Propagating all over the plate surface | " |

Table 7 clearly shows that the subliming propolis solid composition of the present invention contains an active propolis component, natural antimicrobial agent, which is homogeneously incorporated, and that the active propolis component is effectively dissipated around the solid composition.

Application Example 4

A square container having three holes having a diameter of 2.2 cm each on top was charged with 2 kg of the subliming propolis solid composition obtained in Example 1, and placed in a scirocco fan air circulator (having a size of 32 cm×16 cm×18 cm). The air circulator was operated for 6 hours, and then 160 liters of air in a position 2 mm away from the air circulator was collected 1 hour or 6 hours after the initiation of the above operation.

Thereafter, bacteria contained in the collected air were cultured on an agar culture medium at 30° C. for 3 days, fungi contained in the collected air were cultured on an agar culture medium at 25° C. for 7 days, and formed colonies of the microorganisms were counted. Table 8 shows the results.

TABLE 8

| Microorganism | Bacteria | | Fungi | |
|---|---|---|---|---|
| Time period of operation | Bacterial in floating state | Bacteria in fallen state | Fungi in floating state | Fungi in fallen state |
| Before operation | 16 | 6 | 53 | 13 |
| After 1 hour | 2 | 0 | 5 | 4 |
| After 6 hours | 0 | 0 | 2 | 0 |

Table 8 clearly shows that the subliming propolis solid composition of the present invention excellently works to remove microorganisms.

Application Example 5

A cylindrical container having an opening having a diameter of 2.2 cm on top was charged with 300 g of the subliming propolis solid composition obtained in Example 9, and placed in the same air fan (having a size of 8.5 cm×9 cm×24 cm) as that used in Application Example 2. The air fan was operated for 12 hours. A polyester film contaminated with microorganisms was vertically placed 30 cm before the air fan, and colonies of general microorganisms alive per 10 $cm^2$ of the polyester film were measured for a change in their number with a stamp type checkup media. Table 9 shows the results.

TABLE 9

| Microorganism/ Time period of operation | General microorganisms alive (number of colonies/10 $cm^2$) |
|---|---|
| Before operation | 36 |
| After 1 hour | 30 |
| After 6 hours | 24 |
| After 12 hours | 20 |

Table 9 clearly shows that persistently adhering general microorganisms alive in a large quantity are reliably removed with the subliming propolis solid composition of the present invention.

The subliming propolis solid composition of the present invention is produced by mixing a mass formed of a propolis active component and a carrier component, or an extraction residue of the mass, with a water-based micelle solution of a surfactant so as to be brought into contact with each other, to obtain a uniform dispersion, and solidifying the uniform dispersion with a hydrophilic polymer compound. The subliming propolis solid composition is a stable solid as a composition, regularly and continuously dissipates subliming components to give an excellent sense of fragrance and is useful as an atmosphere-ameliorating agent.

According to the present invention, therefore, the role of propolis as a natural antimicrobial and health-improving substance can be applied not only to conventional health beverages but also newly to daily-use articles to be arranged in environments.

What is claimed is:

1. A process for preparing an air freshener propolis solid composition comprising (A) a propolis mass and/or an extraction residue thereof having a surface adapted to absorb a surfactant, (B) water alone or a mixture of water with a water-soluble solvent capable of forming a hydrogen bond with water, (C) an anionic surfactant containing polyacrylate, and (D) a hydrophilic polymer compound, the subliming propolis solid composition containing, per 100 parts by weight of total of components (A) and (B), 0.01 to 25 parts by weight of component (C) and 0.1 to 50 parts by weight of component (D), the process comprising the steps in the order listed of:
(1) preparing a solvent solution by dissolving a surfactant (C) in water alone or a mixture of water with a water-soluble solvent capable of forming a hydrogen bond with water (B) to obtain a solvent solution,
(2) at a temperature of 15 to 200° C., mixing the solution of step (1) with a propolis mass and/or an extraction residue thereof (A) to form a suspension, and then
(3) adding and homogeneously mixing a hydrophilic polymer compound (D) to/with the dispersion of step (2) while the dispersion is maintained at a temperature of 0 to 200° C. and allowing the mixture to stand and solidify into a solid composition.

2. The process of claim 1, wherein the hydrophilic polymer (D) is selected from the group consisting of carrageenan, sugar, agar, starch, polyvinyl alcohol, polyacrylamide, polyethylene oxide, carboxymethyl cellulose, guar gum, xanthane gum, crosslinked polyacrylate, crosslinked polyacrylamide and mixtures thereof.

3. The process of claim 1, wherein hydrophilic polymer compound (D) is carrageenan.

4. The process of claim 1, wherein components (A) and (B) are present in a weight ratio of 1:999 to 1:2.

5. The process of claim 1, wherein the weight ratio of component (A) to component (B) is 1:99 to 1:4.

6. The process of claim 5, wherein the weight ratio of component (A) to component (B) is 1:49 to 1:9.

7. A process of preparing a subliming air freshener propolis solid composition comprising (A) a propolis mass and/or an extraction residue thereof, (B) water alone or a mixture of water with a water-soluble solvent capable of forming a hydrogen bond with water, (C) an anionic surfactant containing polyacrylate, and (D) a hydrophilic polymer compound selected from the group consisting of carrageenan, agar, starch, polyvinyl alcohol, polyacrylamide, polyethylene oxide, carboxymethyl cellulose, guar gum, xanthane gum, crosslinked polyacrylate, crosslinked polyacrylamide and combinations thereof, the subliming propolis solid composition comprising, per 100 parts by weight of total of components (A) and (B), 0.01 to 25 parts by weight of component (C) and 0.1 to 50 parts by weight of component (D), the process comprising the steps in the order listed of:
(1) preparing a solvent solution by dissolving a surfactant (C) in water alone or a mixture of water with a water-soluble solvent capable of forming a hydrogen bond with water (B) to obtain a solvent solution,
(2) at a temperature of 15 to 200° C., mixing the solution of step (1) with a propolis mass and/or an extraction residue thereof (A) to form a suspension, and then
(3) adding and homogeneously mixing a hydrophilic polymer compound (D) to/with the dispersion of step (2) while the dispersion is maintained at a temperature of 0 to 200° C. and allowing the mixture to stand and solidify into a solid composition.

* * * * *